United States Patent [19]
Samson

[11] Patent Number: 4,582,181
[45] Date of Patent: Apr. 15, 1986

[54] STEERABLE DILATATION CATHETER

[75] Inventor: Wilfred J. Samson, Saratoga, Calif.

[73] Assignee: Advanced Cardiovascular Systems, Inc., Mountain View, Calif.

[21] Appl. No.: 522,835

[22] Filed: Aug. 12, 1983

[51] Int. Cl.[4] ............................................. A61M 25/00
[52] U.S. Cl. .................................. 128/348.1; 604/95
[58] Field of Search ................ 128/325, 344, 348–350, 128/1 D; 604/95–103, 282

[56] References Cited

U.S. PATENT DOCUMENTS 4,444,188  4/1984  Bazell .................................. 128/344

Primary Examiner—Robert Peshock
Attorney, Agent, or Firm—Flehr, Hohbach, Test, Albritton & Herbert

[57] ABSTRACT

Low profile dilation catheter and method of manufacturing the same for use in percutaneous transluminal coronary angioplasty. The catheter has an inflatable balloon for dilating stenotic lesions, and an integral guide wire by which the catheter can be steered into the artery system.

15 Claims, 4 Drawing Figures

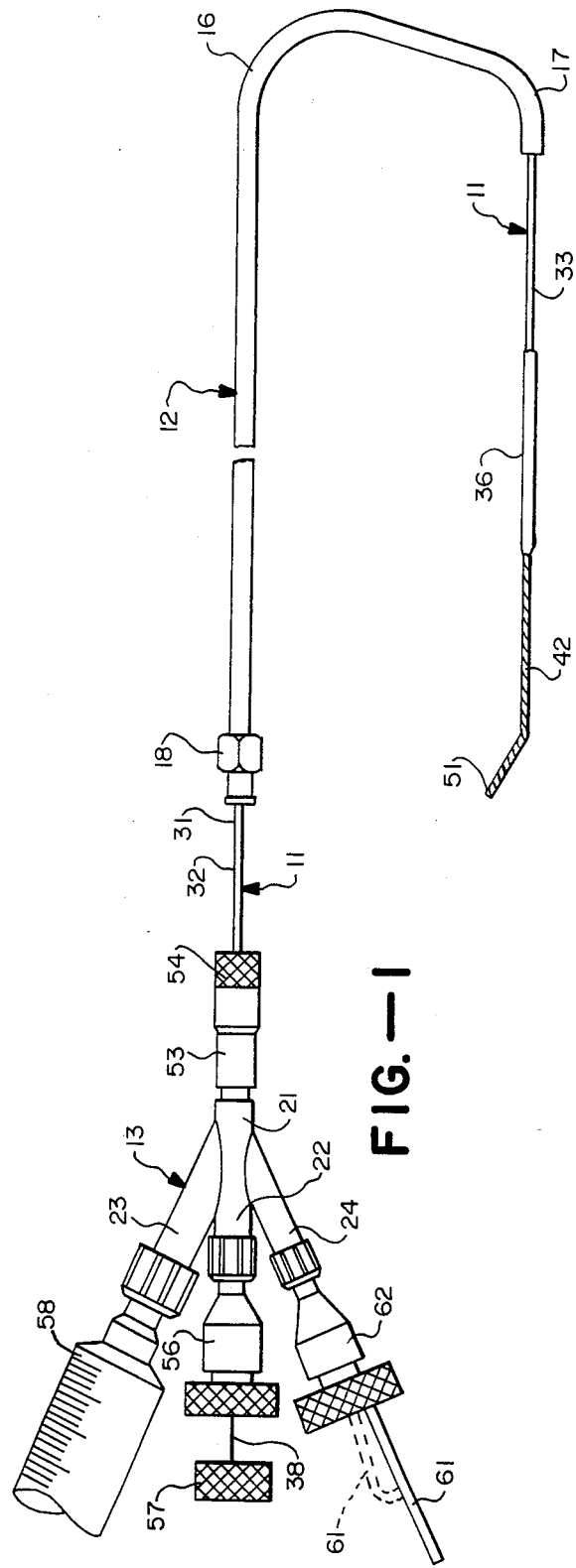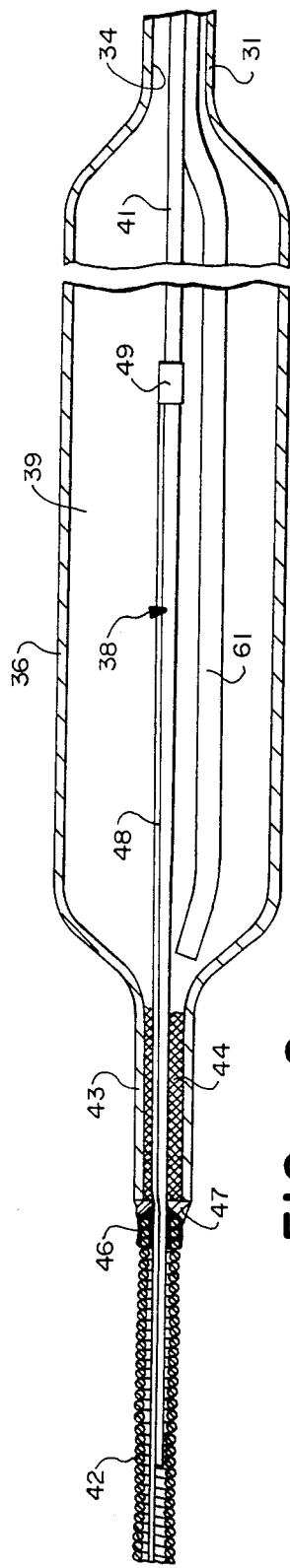

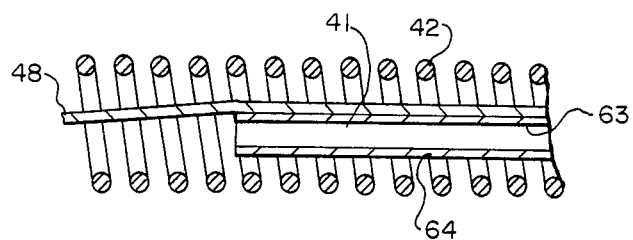
FIG. — 3
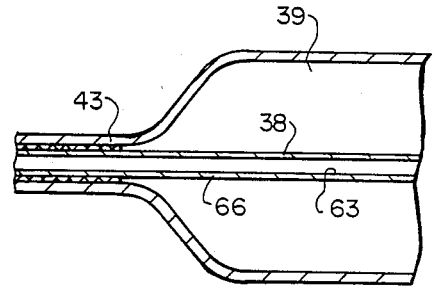
FIG. — 4

STEERABLE DILATATION CATHETER

This invention pertains generally to a dilatation catheter in coronary angioplasty, and more particularly to a steerable dilatation catheter of this type.

In percutaneous transluminal coronary angioplasty, catheters are inserted into the cardiovascular system via the femoral artery under local anesthesia. A preshaped guiding catheter is positioned in the coronary artery, and a dilatation catheter having a distensible balloon portion is advanced through this catheter into the branches of the coronary artery until the balloon portion traverses or crosses a stenotic lesion. The balloon portion is then inflated with a fluid to compress the atherosclerosis in a direction generally perpendicular to the wall of the artery, thereby dilating the lumen of the artery.

U.S. Pat. No. 4,323,071 discloses a dilatation catheter which is advanced along a guide wire to the desired position in the arterial system. The catheter has inner and outer concentric tubular members, with an inflatable balloon formed in the outer tubular member and the tubular members being sealed together at their distal ends. Fluid for inflating the balloon is introduced through the pasageway formed between the tubular members, and the guide wire passes through the central opening or lumen of the inner tubular member. Because of the wall thicknesses of the two tubular members, this type of catheter is difficult to use in some of the smaller arteries and in cases of more advanced stenosis where the artery is closed to such an extent that the catheter cannot be extended through the lesion. There is therefore a need for a low profile balloon type catheter which can be steered through tortuous vessels.

It is in general an object of the invention to provide a new and improved dilatation catheter which can be steered.

Another object of the invention is to provide a catheter of the above character in which the catheter has a relatively low profile or small outer diameter.

Another object of the invention is to provide a catheter and method of the above character in which the catheter can be steered or directed as it is inserted into the cardiovascular system.

Another object of the invention is to provide a catheter of the above character which has a flexible radio opaque tip which can be readily observed in coronary angioplastic procedures.

These and other objects are achieved in accordance with the invention by providing a dilatation catheter having an elongated tubular member with an inflatable balloon toward the distal end thereof, and an integral guide wire extending through the opening in the tubular member. The distal end of the tubular member is bonded to the guide wire to close one end of the balloon and secure the tubular member to the guide wire in a fixed position. Fluid is introduced into the passageway formed between the inner wall of the tubular member and the guide wire to inflate the balloon. The tip of the guide wire extends beyond the balloon and can be shaped to facilitate insertion into a side branch of the artery system.

FIG. 1 is an elevational view of one embodiment of a steerable dilatation catheter according to the invention used in combination with a guiding catheter and a control unit.

FIG. 2 is an enlarged, fragmentary centerline sectional view of the balloon portion and the distal end of the dilatation catheter of FIG. 1.

FIG. 3 is an enlarged, fragmentary centerline sectional view of the distal end portion of another embodiment of a dilatation catheter according to the invention.

FIG. 4 is an enlarged, fragmentary centerline sectional views illustrating still another embodiment of a dilatation catheter according to the invention.

In FIG. 1, the dilatation catheter 11 is illustrated in connection with a guiding catheter 12 and a control unit 13. The guiding catheter can be of any suitable design, and in the embodiment illustrated it is formed with bends 16, 17 toward its distal end for insertion into the left coronary artery. A Luer fitting 18 is provided at the proximal end of the guiding catheter.

Control unit 13 comprises a three arm adapter having a body portion 21 with a central arm 22 and side arms 23, 24 at one end thereof. The proximal end of dilatation catheter 11 is connected to the control unit, and connections to different elements of the catheter are made via the three arms of the adapter.

Dilatation catheter 11 comprises an elongated tubular member 31 having a proximal end 32, a distal end 33 and an axially extending lumen or flow passage 34. An inflatable balloon 36 is provided toward the distal end of the tubular member. The tubular member is fabricated of a flexible, elastic material such as a heat shrinkable polyethylene, and in the embodiment illustrated the balloon is formed as an integral part of the tubular member by distending a portion of the wall of the member.

A guide wire 38 extends axially through the luminal opening 34 of tubular member 31 and the chamber 39 of balloon 36, with the proximal and distal ends of the guide wire projecting beyond the corresponding ends of the tubular member. The guide wire comprises an elongated shaft 41, with a flexible helical coil 42 extending axially from the distal end of the shaft. A portion 43 of tubular member 31 is sealed directly onto the guide wire shaft at the distal end of balloon 36, whereby balloon chamber 39 is closed at its distal end and the tubular member is affixed to the guide wire to form a unitary structure. At its proximal end, balloon chamber 39 is in direct fluid communication with the passageway 34 formed between the inner wall of tubular member 31 and guide wire shaft 41. In the embodiment illustrated, balloon 36 is approximately 24 mm long, and the end portion 43 of the tubular member which is sealed onto the guide wire is approximately 5 mm long. In this particular embodiment, the tubular member is sealed to the guide wire by a suitable adhesive 44 such as an epoxy material. However, it will be understood that the end portion of the tubular member can be affixed to the guide wire by other suitable means to seal the distal end of the balloon. Such means include direct fusion of the tubular member to the guide wire, and the use of a clamp to secure the tubular member to the guide wire.

Helical coil 42 begins just beyond the distal end of tubular member 31. It is affixed to shaft 41 by suitable means such as epoxy 46. A filler material 47 such as an expoxy is employed in the region between the end of the tubular member and the beginning of the helical coil to provide a smooth transition between the tubular member and the coil.

The distal end portion of guide wire shaft 41 is tapered to provide a gradual transition in flexibility between the shaft and the relatively flexible helical coil 42. In the embodiment illustrated, shaft 41 has a diameter of 0.010 inch between its proximal end and the proximal end of balloon 36, tapering to a diameter of 0.004 inch at the proximal end of coil 42. The shaft extends about 5-10 mm into the coil. Coil 42 has a diameter on the order of 0.018 inch, and is fabricated of a suitable material having a high radio opaque density such as platinum, tungsten, tantalum and gold preferably in an alloy form to give the desired spring characteristics. A safety ribbon or wire 48 extends between the distal end portions of shaft 41 and helical coil 42. This wire is fabricated of a material which is stronger than the helical coil, and in one presently preferred embodiment it comprises a flat tungsten ribbon having a thickness of about 0.001 inch and a width of about 0.003 inch. In this embodiment, the safety wire extends from a point midway through the balloon to the distal end of the helical coil. The end portions of the safety wire are affixed to shaft 41 and to the distal end of the coil by suitable means such as brazing. Alternatively, the proximal end portion can be fixed to the shaft 41 under band 49. The brazing can be done with a radio opaque material such as gold or a gold alloy to form markers in the form of a gold band 49, and in the form of a ball 51 having a rounded ball-like configuration which are visible to a fluoroscope. Marker 51 provides a smooth tip at the distal end of the guide wire. The safety wire if desired also may be bonded to the guide wire by brazing at 46, and a radio opaque material can also be utilized here to provide an additional marker. If additional flexibility is desired in the coil, the safety wire can be omitted. The gold band marker 49 and the ball-like tip 51 could be retained.

Catheters manufactured in accordance with the invention have a significantly lower profile, i.e. smaller diameter, than dilatation catheters heretofore provided. In one presently preferred embodiment, balloon 36 has a diameter of 2.0 mm when inflated, and tubular member 31 has an outside diameter of 0.035 inch with a luminal opening of 0.024 inch. In another embodiment, the inflated balloon has a diameter of 2.5 mm, and tubular member 31 has an outside diameter of 0.035 inch and a luminal opening of 0.023 inch. In a third embodiment, the inflated balloon has a diameter of 3.0 mm, and tubular member 31 has an outside diameter of 0.042 inch and a luminal opening of 0.021 inch. These dimensions are exemplary only, and it will be understood that the catheter can have any suitable dimensions.

At the proximal end of the catheter, tubular member 31 is connected to the body of control unit 13 by means of connectors 53, 54, with the luminal opening 34 of the tubular member in communication with the interior of the adapter body. The proximal end of guide wire 38 extends through central arm 22 and a valve assembly 56 which is connected to the central arm. The valve assembly includes an O-ring which forms a fluid-tight seal with the guide wire, while permitting rotation of the guide wire about its axis. A control knob 57 is attached to the proximal end of the guide wire outside the adapter and valve assembly. Side arm 23 communicates with the luminal opening 34 of the tubular member, and a syringe 58 is attached to side arm 23 for intorducing radio opaque fluids into the luminal opening.

A vent tube 61 extends through the luminal opening 34 of tubular member 31 and communicates with the chamber 39 of balloon 36. The proximal end of the vent tube 61 is connected to side arm 24 and communication with this end of the vent tube is controlled by a valve assembly 62 connected to side arm 24.

Operation and use of the dilatation catheter can now be described. Guiding catheter 12 is positioned in the coronary artery, and prior to insertion into the guiding catheter, dilation catheter 11 is connected to control unit 13. The vent tube is introduced into the position shown in FIG. 2. A suitable fluid such as a radiographic contrast liquid is introduced into the catheter by syringe 58 to fill balloon 36 and expel any air in the balloon and the passageway leading thereto out through vent tube 61 and valve 62. The proximal end of the vent tube 61 is reversed onto itself and inserted into the vent valve 62 as shown by the broken lines which is then closed to form a seal. The contrast medium is withdrawn to deflate the balloon. The deflated balloon can be wrapped in helical fashion about guide wire 31 to reduce the profile of this portion of the catheter, if desired, and the distal end portion of the guide wire can be bent or shaped to facilitate insertion into a side branch of the artery system.

The dilatation catheter is inserted into the coronary artery through the guiding catheter and advanced until balloon 36 traverses or crosses the lesion to be dilated. The catheter is steered as it is inserted by turning control knob 57, and the position of the balloon is determined by monitoring markers 49, 51 with a fluoroscope. When the balloon traverses the lesion, pressurized fluid (e.g., contrast medium) is introduced by syringe 58 to inflate the balloon and compress the atherosclerosis. Upon completion of the dilatation process, the balloon is deflated, and the catheters are withdrawn.

In the embodiment of the catheter illustrated in FIG. 3, the shaft 41 of guide wire 38 is a hollow having an axially extending passageway 63 formed therein. A port 64 is formed in the side wall of the hollow wire and communicates with passageway 63. In this embodiment, port 64 is located in the portion of the shaft which extends into helical coil 42, and pressure measurements can be made ahead of the balloon through the wire. In the embodiment of the catheter shown in FIG. 4, a port 66 is provided in the hollow guide wire 38 and is located within the balloon chamber. The vent tube 61 is eliminated because the balloon can be vented through the hollow wire 38. It is apparent from the foregoing that a new and improved dilatation catheter and method of manufacturing the same have been provided. While only certain presently preferred embodiments have been described in detail, as will be apparent to those familiar with the art, certain changes and modifications can be made without departing from the scope of the invention as defined by the following claims.

I claim:

1. In a dilatation catheter, an elongate flexible plastic tubular member having proximal and distal ends and an axially extending flow passage extending therethrough, an inflatable balloon of flexible plastic carried by the tubular member and disposed near the distal end of the tubular member and having its interior in communication with the flow passage, a continuous guide wire extending through the flow passage, the balloon and the distal end of the tubular member, and means bonding the distal end of the tubular member directly to the guide wire to form a bond so that the guide wire is secured to the distal extremity of the tubular member.

2. The dilatation catheter of claim 1 wherein the balloon is formed as an integral part of the tubular member.

3. The dilatation catheter of claim 1 together with a vent tube extending through the flow passage in the tubular member and into the interior of the balloon.

4. The dilatation catheter of claim 1 wherein the guide wire comprises a hollow wire having an axially extending passageway and a port which communicates with the passageway and the balloon chamber for venting the chamber.

5. The dilatation catheter of claim 1 wherein the balloon is sealed to the guide wire with an adhesive.

6. The dilatation catheter of claim 1 together with a flexible coil secured to the distal extremity of the guide wire.

7. The dilatation catheter of claim 6 wherein the flexible coil is formed of a radiopaque material.

8. In a catheter for dilating a lesion in the cardiovascular system, an elongate flexible plastic tubular member having proximal and distal ends and an axially extending flow passage, an inflatable balloon of flexible plastic carried by the tubular member adjacent the distal end of the tubular member and having its interior in fluid communication with the flow passage in the tubular member, a metal guide wire having a shaft which extends through the flow passage in the tubular member and into the interior of the balloon, means directly bonding the distal end of the tubular member to the guide wire, means connected to the proximal end of the guide wire for rotating the same to steer the catheter into the cardiovascular system, and means connected to the proximal end of the tubular member for introducing a pressurized fluid into the flow passage to inflate the balloon.

9. The catheter of claim 8 wherein the guide wire includes a flexible coil affixed to the shaft near the distal end of the tubular member and extends beyond the tubular member to form a flexible tip.

10. The catheter of claim 9 wherein the distal end portion of the guide wire shaft extends axially into the coil and is tapered to provide a gradual transition in flexibility between the shaft and the coil.

11. The catheter of claim 10 wherein the shaft terminates prior to the distal end of the coil together with a flexible safety wire extending between the shaft and the distal end of the coil and means securing said safety wire to the shaft and to the distal end of the coil.

12. The catheter of claim 9 wherein the distal end of the coil is ball-like.

13. The catheter of claim 11 wherein the means securing the safety wire to the distal end of the coil has a ball-like configuration.

14. The catheter of claim 9 together with a marker of radiopaque material affixed to the guide wire within the balloon catheter.

15. The catheter of claim 9 wherein the flexible helical coil is formed of a radiopaque material.

* * * * *